(12) United States Patent
Hiromoto

(10) Patent No.: US 6,517,851 B1
(45) Date of Patent: Feb. 11, 2003

(54) REDUCING NEMATODE INFESTATION WITH FUNGI TREATED OIL HAVING NEMATICIDAL ACTIVITY

(75) Inventor: Bryan Hiromoto, Pukalani, HI (US)

(73) Assignee: ABR, LLC, Honolulu, HI (US)

( * ) Notice: Subject to any disclaimer, the term of this patent is extended or adjusted under 35 U.S.C. 154(b) by 0 days.

(21) Appl. No.: 09/327,346

(22) Filed: Jun. 5, 1999

Related U.S. Application Data

(62) Division of application No. 09/103,646, filed on Jun. 23, 1998, now Pat. No. 6,048,714.
(60) Provisional application No. 60/050,583, filed on Jun. 24, 1997.

(51) Int. Cl.$^7$ .......................... A01N 25/00; A01N 63/00; A01N 63/04; C12N 1/00; C12N 1/14
(52) U.S. Cl. ...................... 424/405; 424/93.3; 424/93.5; 424/93.51; 424/115; 435/254.1; 435/255.1; 435/911
(58) Field of Search ................................ 424/405, 93.1, 424/93.3, 93.5, 93.51, 115; 435/254.1, 255.1, 911

(56) References Cited

U.S. PATENT DOCUMENTS

| | | | |
|---|---|---|---|
| 4,536,207 A | * 8/1985 | McCandliss et al. | 71/88 |
| 4,958,011 A | * 9/1990 | Bade | 536/20 |
| 5,162,349 A | * 11/1992 | Beriger et al. | 514/363 |
| 5,639,794 A | * 6/1997 | Emerson et al. | 514/699 |
| 5,989,543 A | * 11/1999 | Davidé et al. | 424/93.5 |

FOREIGN PATENT DOCUMENTS

| | | |
|---|---|---|
| EP | 0354491 A2 * | 2/1990 |
| EP | 0623284 A1 * | 11/1994 |

OTHER PUBLICATIONS

U Reference: Stadler et al., "Fatty acids and other compounds . . . ", Planta Media, vol. 60, No. 2, pp. 128–132, 1994.*

Anke et al., Can. J. Bot. 73 (Supple. 1):S932–S939 (1995).
Hayashi et al., Agric. Biol. Chem 45(6):1527–1529 (1981). Abstract.
Kawazu et al., Biosci., Biotechnol., Biochem. 57(1):98–101 (1993). Abstract.
Kloepper, J.W. et al., "Development of a Powder Formulation of Rhizobacteria for Inoculation of Potato Seed Pieces," *Phytopathology* 71:590–592 (1981).
Mayer et al., Med. Fac. Landbouww Univ. Gent. 61(3a):839–847 (1996).
Mishra et al., J. Ind. Microbiol. 2(5):267–276 (1987). Abstract.
P. Vidhyasekaran et al., "Development of Formulations of *Pseudomonas Fluorescens* for Control of Chickpea Wilt," *Plant Dis.* 79: 782–786 (1995).
Shimizu, *J. Natural Products* 48:223–235 (1985).
Stadler et al., Journal of Antibiotics 47(11):1284–1289 (1994). Abstract.
Stadler et a., Planta Medica 60(2):128–132 (1994). Abstract.
Stadler et al., Natural Product Letters 7:7–14 (1995).
Stadler et al., Z. Naturforsch. 50:473–475 (1995).
Townshend et al., *J. Nematology* 21:179–183 (1989).

* cited by examiner

Primary Examiner—David M. Naff
Assistant Examiner—Deborah K. Ware
(74) Attorney, Agent, or Firm—Morrison & Foerster LLP

(57) ABSTRACT

A pesticide composition that includes a metabolite from a fungus selected from homeocarpic basidiomycetes and homeocarpic ascomycetes is produced. In one embodiment, the fungus from which the metabolite is derived is one grown under conditions effective to substantially suppress fruiting of the fungus. More particular the pesticide compositions are provided comprising a fungal metabolite derived from a fungus selected from the group Ganoderma spp., Lactiporus spp. Lentinus spp. Morchella spp., and Pleurotus spp. The pesticide composition may be produced by culturing the fungus on a medium containing vegetable oil and a surfactant. Alternatively a filtrate from a culture of the fungus is added to the medium containing vegetable oil and a surfactant, and mixed until pesticidal activity develops.

14 Claims, 3 Drawing Sheets

REDUCING NEMATODE INFESTATION WITH FUNGI TREATED OIL HAVING NEMATICIDAL ACTIVITY

CROSS REFERENCE TO RELATED APPLICATION

This application is a divisional application of U.S. Ser. No. 09/103,646 filed Jun. 23, 1998 which is now issued as U.S. Pat. No. 6,048,714 which application claims priority under 35 U.S.C. §119(e) from provisional application No. 60/050,583 filed Jun. 24, 1997, both incorporated herein by reference.

FIELD OF THE INVENTION

The present invention relates to compositions having pesticidal properties, methods for obtaining such compositions, and methods for using such compositions. More particularly, the present invention provides compositions having nematicidal properties, as well as methods for obtaining and using such compositions. The present invention thus includes applications in the areas of agriculture as well as veterinary and human medicine.

BACKGROUND

Nematodes, commonly referred to as "roundworms", comprise a phylum of about 12,000 species of unsegmented terrestrial, freshwater, or marine worms. Both saprophytic and parasitic forms are known. Parasitic nematodes are recognized as having either needle or odonto (tooth-like) stylets. Nematodes are abundant in the surface layers of soils and are found throughout the world. They are recognized by having cylindrical, tapering, simple bodies that comprise an interior gut and a muscular outer wall that are separated by a fluid-filled cavity. Nematodes range in size from microscopic to about 10 cm (about 4 in) long. A few species are hermaphroditic, but most have separate sexes.

Nematodes have raised great economic and humanitarian concern due to their impact on the world's agricultural output as well as their impact on human and animal suffering and disease. Regarding the impact nematodes have on agriculture, annual world-wide losses resulting from nematode infestation have been estimated to be about $78 billion. In the United States alone, annual losses due to nematode-related crop diseases are estimated to be about $8 billion. The impact on a crop production by a single nematode-related pathogen can be severe. For example, the soybean cyst nematode causes annual losses of about $267 million in the north central United States; $38 million in state of Missouri alone.

Tomatoes and strawberry production are often the agronomic crops most severely impacted by nematode infestation. Control of nematode infestation of these crops historically has depended on low cost, highly effective chemicals including methyl bromide ($CH_3Br$), ethylene dibromide ($C_2H_4Br_2$, "EDB"), and 1,2-dibromo-3-chloropropane ($C_3H_5Br_2Cl$, "DBCP"). However, the application of these workhorse pesticides has been or will soon be banned by governmental regulatory agencies for their unwanted health and environmental impacts. The resulting economic impacts from these bans will be severe. The National Pesticide Impact Assessment Program ("NAPIAP") has estimated annual economic losses of $1.3 to $1.5 billion in the United States from a ban on the agricultural use of methyl bromide. In California, for example, the Office of Pesticide Consultation and Analysis of the California Department of Food and Agriculture estimated in 1996 that economic damages resulting from a ban on using methyl bromide will result in crop losses totaling between about $287 and $346 million, in addition to $241 million in trade income. Estimates of more than $500 million in crop losses are projected for Florida. See Spreen, T. H., et al., *Bull. Univ. Fla. Exp. Stn. No.* 898 (1995).

Unfortunately, no truly viable successor to methyl bromide, EDB, or DBCP has been found. The pesticides sold commercially under the tradenames Temik and Dazomet have limited registration. Other commercially available pesticides, such as those sold under the tradenames Carbofuran, Vapam, and Chloropicrin, have limited effectiveness. Still other nematicides have been shown to be carcinogenic (e.g., the pesticide sold as Telone). Recently the pesticides sold under the names Aldicarb and Carbofuran have lost registration. Development of new chemicals having effective nematicidal applications in the near future appears remote; in fact, no new nematicide has been developed since 1974.

Non-pesticide alternatives to nematode control have been disappointing. Pre-plant fumigation alternatives do not provide the same level of nematicidal effectiveness as methyl bromide. Several fungal parasites of nematodes have been reported, but none of these has been developed into a commercial product. Morgan-Jones and Rodriguez-Kabana, Vistas on Nematology Ch. 14, 1987; Kerry, Biological Control in Crop Production Ch. 5 (1981). In particular, the use of these fungi for nematode control has not resulted in significant improvement of plant growth. See, e.g. Townshend, et al., 21 *J. Nematology* 179–183 (1989). This failure is probably inherent from the mechanisms used by fungi to kill nematodes. Many of these fungi rely on the migration of the nematode into a trapping structure present in the fungus. Thus, the effectiveness of the fungus' nematicidal activity depends critically on the relatively random occurrence of two different organisms coming in proximity of each other. Such a mechanism of nematicidal action has little effect on endoparasitic or sedentary nematodes.

Nematodes also cause human and animal suffering and/or death. Medically significant forms of nematode include the various genera known as hookworm, the filaria of which cause elephantiasis; and the trichina worm, the cause of trichinosis. Heartworm and pinworm are still other nematode species that cause debilitating disease and death, especially in animals such as dogs, cats, horses, and cattle. In food animals, e.g, pigs and cattle, nematode (worm) infection significantly reduces meat/dairy production efficiency since the infected producing animal requires greater quantities of feed to produce the same amount of food as an uninfected animal. Generally, ivermectin is the leading treatment for worm infection in horses and cattle. Howver, ivermectin is expensive.

Thus, a serious need exists for new and effective compositions and strategies to control nematode infestation. The present invention meets these and other important needs.

SUMMARY OF THE INVENTION

The present invention provides needed and important pesticide compositions and methods for obtaining such compositions. In an important aspect, the compositions provided by the present invention have pesticide activity against nematodes, i.e., the compositions are nematicides. The nematicides of the present invention have activity similar to commercially available nematicides, but have been found to be biodegradable; thus more compatible with environmental and exposure concerns.

In one aspect, the present invention provides a pesticide composition that comprises a metabolite from a fungus selected from the group of homeocarpic basidiomycetes and homeocarpic ascomycetes. In one embodiment, the fungus from which the metabolite is derived is one grown under conditions effective to substantially suppress fruiting of the fungus. More particular embodiments include pesticide compositions comprising a fungal metabolite from a fungus selected from the group Ganoderma spp., Laetiporus spp., Lentinus spp., Morchella spp., and Pleurotus spp.

In another embodiment, the pesticide composition comprises a metabolite obtained by culturing a fungus from a fungal genus selected from the group consisting of homeocarpic basidiomycetes and homeocarpic ascomycetes under culture conditions effective to inhibit substantially fruiting of said fungus. More particular embodiments includes those wherein the fungus is cultured in a culture medium having a low nitrogen content. The nitrogen content in one embodiment is less than about 0.5% by weight. In another embodiment, the nitrogen content is between about 0.1% by weight and about 0.01% by weight. Other embodiments includes those for which the fungus is cultured under a low oxygen partial pressure. Exemplary embodiments include those for which the oxygen partial pressure is less than about 5.0%, and, more particularly, is about 1.0%

In another aspect, the present invention provides a growth medium that has been found to be useful in generating the pesticide composition of the invention. More particularly, the pesticide generated is a nematicide. In one embodiment, the culture medium has the following composition:

| | |
|---|---|
| Ground oatmeal | 15 g/l |
| Brewer's yeast | 15 g/l |
| Corn gluten | 15 g/l |
| Molasses | 3 tsp./l |
| Citric acid | 6 g/l |
| Water | 3 l |
| Vegetable oil | 2 ml/l |

In another embodiment, the culture medium includes an oil or oil mixture having a Saturation Index of less than about 1.0, and, more particularly, less than about 0.5. In another aspect, the present invention provides methods for reducing or preventing plant damage resulting from nematode infestation in which an effective amount of the composition of the invention is delivered to a plant in need of such treatment.

These and other aspects and advantages of the present invention will become more apparent when the Description below is read in conjunction with the accompanying

DESCRIPTION OF SOME SPECIFIC EMBODIMENTS

Figure 1:
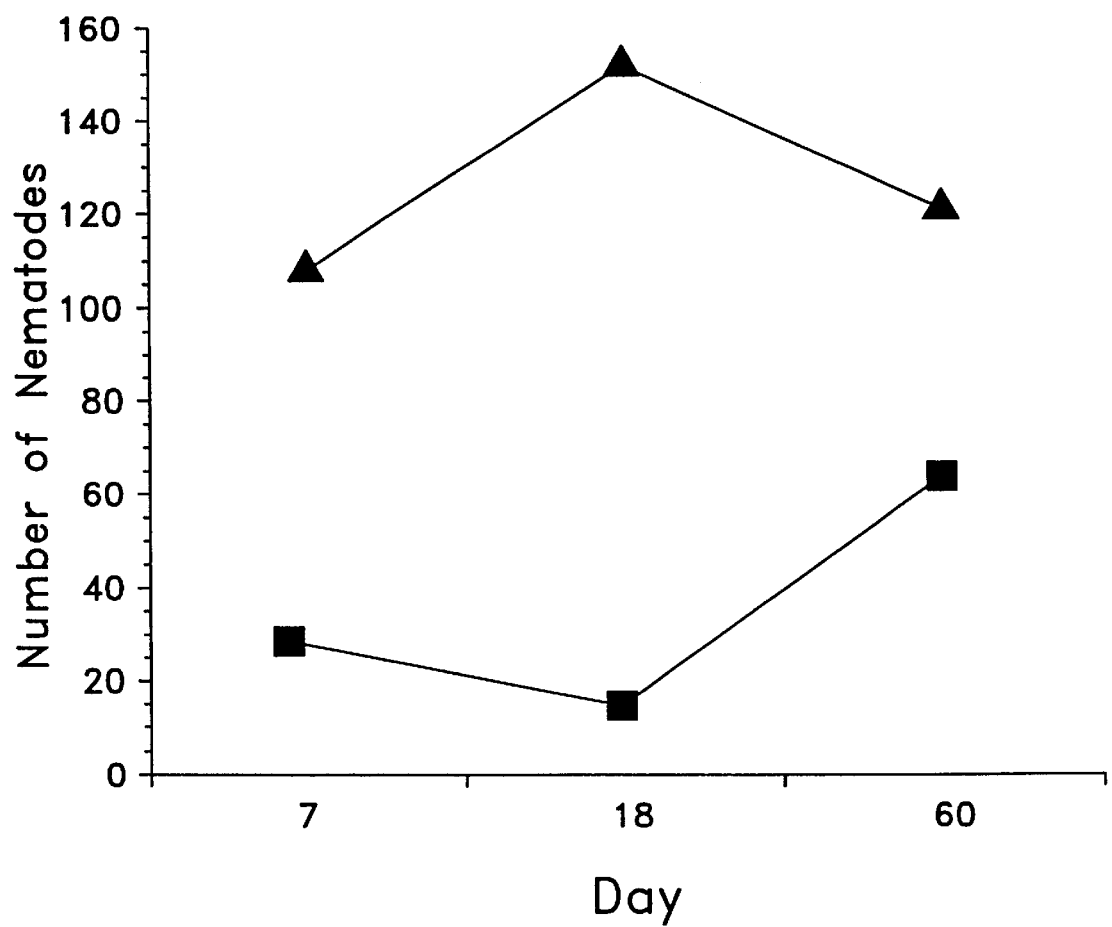
FIG. 1 is a graph showing the effect of a 1:5,000 dilution (w/Dawn® detergent at 1:800) of Laetiporus-treated safflower oil (■) on reniform nematodes versus a control (▲).

The present invention provides a novel growth medium and growth conditions for the culture of fungi, more particularly fungi derived from the genera basidiomycetes and ascomycetes. In particular, it has been found unexpectedly that culturing fungi derived from the aforementioned basidiomycetes and ascomycetes genera in the growth medium and growth conditions provided herein provides a fungal metabolite that has pesticidal, and, more particularly, nematicidal, effectiveness similar to that of nematicides such as methyl bromide, EDB, NEMACUR®, and DBCP. However, unlike nematicides used presently, the pesticidal composition provided by the present invention appears to be biodegradable for the reasons described hereinbelow.

Thus, the present invention provides a pesticidal composition having desirable qualities for the control of nematode infestations in addition to infestations by other pest species. In addition, the compound(s) that provides the pesticidal, and, more particularly, nematicidal, properties of the composition of the present invention can be a basis for the development of chemical analogs having unique and desirable pesticidal properties. Furthermore, the materials and methods described herein can be used to identify and develop genetic variants of the fungi described hereinbelow to provide additional pesticidal compositions, compounds, and methods using known molecular biological and genetics techniques. In addition, the materials, media, and methods of the invention can be used as to evaluate other species of fungi for the production of nematicidal activity as well as a basis against which to compare other media formulations and culture conditions for the production of pesticides, and nematicides more generally.

Fungal Growth Medium/Conditions for Producing Nematicidal Compositions

In one aspect, the present invention provides methods, growth media, and growth conditions for producing nematicidal compositions. Using the methods, media, and conditions described herein, insecticide compositions having significant nematicide activity (in addition to other types of pesticide activity) can be obtained.

Growth Conditions

In one embodiment, the present invention provides a pesticide composition obtained by culturing fungi of the homeocarpic basidiomycetes and ascomycetes genera under conditions that prevent substantial fruiting of the fungi. In another embodiment, the pesticide composition is obtained by culturing homeocarpic basidiomycetes and ascomycetes fungi under conditions that promote mycelial growth. Such conditions are known to those of skill in the art of culturing fungi, and include, but are not limited to, growing the fungi in media having a low nitrogen content. As used herein, "low nitrogen content" describes materials having a nitrogen content of less than about 0.5% by weight, more particularly less than about 0.2% by weight, still more particularly, between about 0.01% and about 0.1% by weight, and yet more particularly, between about 0.03% and about 0.1% by weight. Examples of low nitrogen conditions include growth under increased carbon dioxide ($CO_2$) partial pressure. Suitable $CO_2$ partial pressure can be achieved by maintaining a low oxygen ($O_2$) partial pressure in the culture conditions. Such culture conditions include those wherein the $O_2$ partial pressure (expressed as a percentage) is between about 0.1% and about 5.0%, more particularly between about 0.1% and about 2.0%, still more particularly between about 0.1% and about 1.0%. In one embodiment, the partial pressure of $O_2$ is maintained at a level of about 1.0%. Such conditions can be achieved by culturing the fungi on decaying wood, especially decayed or decaying wood taken from wooden telephone poles. See, Wang and Zabel, Identification Manual for Fungi From Utility Poles in the Eastern United States 356 (1990). In still other embodiments, the desired low nitrogen conditions are provided by the growth media described hereinbelow.

Still other conditions that are known to repress fruiting include darkness, adjustment of temperature. For example, temperatures of less than about 27° C., more particularly between about −10° C. and about 27° C., and, still more particularly, between about −10° C. and about +10° C. are useful in obtaining pesticidal, more particularly, nematicidal, activity. In one embodiment, the fungi are cultured in a culture medium having a pH range of between about 3.0 and about 6.0. For example *Laetiporeus sulphureus* basidiocarp has a pH of 3.5. In addition, it has been found that culture conditions that favor the production of oxalic acid ($HO_2CCO_2H$) correlate with increased pesticidal, and particularly nematicidal, properties. Thus, in another embodiment, the culture medium pH is controlled using citric acid, since one of the metabolic products of the citric acid cycle is oxalic acid. Those of skill in the fungus culture arts will recognize that in such embodiments the citric acid adjusts media pH and acts as a nutrient.

Conditions that promote mycelial growth will be familiar to those of skill in the fungus culturing arts. Such conditions include growing fungi under light at wavelengths that are absorbed by β-carotene. Mycelial growth can be further enhanced by culturing the fungi in the presence of β-carotene and/or other suitable substances that have absorb light at a wavelength substantially similar to the absorption wavelength of β-carotene. These nutrients can be provided either by direct supplementation of the culture media or by using nutrient sources that are rich in β-carotene (or similar compound). For example, β-carotene source may be obtained from corn gluten, carrots or yellow squash. Corn gluten also acts as a protein source.

In an alternative embodiment the fungi are allowed to undergo fruiting while being cultured in liquid growth medium, such as a growth medium illustrated below. However, to improve the nematicidal qualities of the isolated composition, the fungi are subjected to cold shock prior to the isolation of the nematicide composition. As used herein, the term "cold shock" refers to a series of fluctuations in culture temperature that are effective to induce increased lipid storage by the fungi in culture by causing an increase in the mycelial mass of the fungi. Such conditions will be familiar to those of skill in the fungus culture arts. For example, shiitake are cultured at room temperature for vegetative growth. To "cold shock" the shiitake, a series of temperature fluctuations comprising a 15° C. temperature drop over a period of about 24 hours followed by a return to room temperature are performed daily over a period of about 30 days prior to fruiting.

Solid Culture Supports

Basidiomycetes and ascomycetes fungi can be grown on solid culture supports to produce the pesticide composition of the invention. As discussed above, those solid growth media known in the art for culturing such fungi can be used where the conditions employed are effective to prevent or retard substantial fruiting of the fungi. Solid agar plates can also be used for cultivation. Alternatively, solid growth media comprising matter having low nitrogen content, such as the wood of decaying telephone poles, can be used without substantially modification of the growth conditions.

Exemplary solid growth supports are shown in below. A variety of growth supports are encompassed by the ranges provided in the "Quantity" column of the Table. In particular, it will be noted that some items, such as the solid carrier, can be in amounts ranging from "0%" to "100%" indicating that the item can be either omitted entirely or used as the sole nutrient source. In general, suitable nutrient supports require only a carbon source, a nitrogen source, a vitamin source and water. The composition used to obtain the best results, i.e., the most efficient production of pesticidal composition, will depend on the type of fungi being cultured and other conditions applicable to the culture (e.g., light, temperature, humidity, and the like). These can be determined by those skilled in the art of culturing fungi using known methods and materials.

In one embodiment, the major component of the solid support is a grain having a protein content of no greater than about 7%–14%. Examples of such gains include sorghum and barley. In another embodiment, the protein content of the grain is about 2%, such as found in bagass (the residual material following the extraction of sugar from sugarcane). By way of example, the medium is prepared by mixing the components and packing the mixture in a sterilizable plastic bag with an air-permeable filter. The mixture is then autoclaved at a temperature and pressure sufficient to substantially sterilize the mixture, e.g., 15 pounds per square inch (psi) and a temperature of 121° C. The duration of autoclaving varies with amount of substrate and can be determined using standard techniques for culturing fungi. For example, a 4,000-pound substrate mixture requires about 9 hours of autoclaving. Such parameters can be determined using known methods.

TABLE 1

| Components | Quantity |
| --- | --- |
| Solid carrier: bagasse, sorghum or other grains or plant materials effective to provide a source of cellulose, i.e., legume seeds, grass seed, barley, wheat, rye, corn, or soybean, straw, wood chips, fir bark. | 0–100% |
| Molasses | 0–100 ml |
| Oatmeal | 0–150 g |
| Sucrose or dextrose, fructose, etc. | 0–120 g |
| Yeast Extract | 0–40 g |
| Bacto-Peptone or proteose peptone, beef extract, etc. | 0–50 g |
| Malt extract | 5–100 g |
| Calcium carbonate | 0–50 g |
| Water | 50% of the water-holding capacity of the solid carrier. |

Liquid Culture Media

Alternatively, liquid culture media can be used to obtain the pesticidal composition of the invention. As discussed above, any culture suitable for growing basidiomycetes and ascomycetes fungi can be used if done under conditions effective to prevent or suppress fruiting of the fungi. Alternatively, temperate fungi can be allowed to undergo fruiting, but a cold shock should be applied to obtain good nematicidal activity.

As will be familiar to those having skill in the art of culturing fungi, the culture media can be "defined" or "undefined", depending on the degree to which the actual chemical compositions of the components of the media are known. The present invention provides both defined and undefined media that are effective to produce fungal metabolites that have pesticidal effectiveness, and, more particularly, nematicidal effectiveness. In one embodiment, the defined and undefined media of the invention are formulated to provide the fungi with growth conditions that have a low nitrogen content and environmental conditions that are effective to suppress substantial fruiting of the fungi and thereby enhance production of pesticide compositions.

Defined Media

In one embodiment, the invention provides defined media effective to support the growth of pesticide-producing fungi. As discussed above, the media can be any used to culture the fungi of interest, provided that either culturing is performed under conditions effective to suppress fruiting of the fungi, or the media has a low nitrogen content. In one embodiment, the present invention provides defined media that have such a low nitrogen content.

Generally, the media of the invention include a carbon source, such as a carbohydrate, e.g., a sugar. Suitable sugars include, without limitation, glucose, dextrose, and maltose. Still others will be familiar to those of skill in the fungs culture arts. In addition, a source of potassium is provided. Examples of useful potassium sources include, without limitation, potassium phosphate ($K_2PO_4$), sodium phosphate ($Na_2PO_4$), and calcium phosphate ($CaPO_4$). A nitrogen source is provided using substances such as, for example, ammonium sulfate (($NH_4)_2SO_4$), ammonium chloride ($NH_4Cl$), or urea ($CO(NH_2)_2$). Other mineral sources are provided such as potassium chloride (KCl), sodium chloride (NaCl), and potassium nitrate ($KNO_3$); manganous sulfate ($MnSO_4$) or manganous oxide (MnO); ferrous sulfate ($FeSO_4$); zinc sulfate (e.g., as the heptahydrate $ZnSO_4 \cdot 7H_2O$); and a co-enzyme such as thiamine. The components are combined in a ratio that supports the growth of the fungi and the production of the pesticidal fungal metabolite. In one embodiment, the combination of medium components provides a carbon:nitrogen ratio of about 100:1. Other equivalent substances will be familiar to those of skill in the cell culture arts. In addition, substances such as agar, agarose, pectin, gelatin, starch, or other artificial solidifying agents may be used from 0–50% (weight/final volume of medium) for production of culture plate media for growing fungi.

Examples of ranges for preparing the media of the invention are provided in Table 2 below. Specific formulations can be found below. In general, the substances are combined using known materials and techniques. The fungi are cultured on the medium so prepared using standard methods and materials as will familiar to those having skill in the fungus culture arts.

TABLE 2

| Component for Defined Medium | Concentration Range (g/l) |
| --- | --- |
| Glucose ($C_6H_{12}O_6$) | 1.0–100.0 |
| $K_2HPO_4$ | 0.01–50.0 |
| $(NH_4)_2SO_4$ | 0.03–30.0 |
| $MgSO_4 \cdot 7H_2O$ | 0.05–50.0 |
| KCl | 0.05–50.0 |
| $MnSO_4$ | 0.002–40.0 |
| $FeSO_4$ | 0.002–40.0 |
| $ZnSO_4 \cdot 7H_2O$ | 0.002–40.0 |
| Thiamine | 0.0001–40.0 |

Undefined Media

In another embodiment, the invention provides undefined media for supporting the culture of fungi under conditions effective to provide pesticide, and, nematicide, fungal metabolites. The general requirements for providing the components of the undefined media are substantially identical to those discussed above. Other equivalent substances will be familiar to those of skill in the cell culture arts.

Examples of ranges for preparing the media of the invention are provided in Table 3 below. Specific formulations can be found below. In general, the substances are combined using known materials and techniques. The fungi are cultured on the medium so prepared using standard methods and materials as will familiar to those having skill in the fungus culture arts.

TABLE 3

| Components Undefined Medium | Range |
| --- | --- |
| Ground oatmeal | 0.1–60 g/l |
| Brewer's yeast or yeast extract | 0.1–15 g/l |
| Corn gluten, corn meal, wheat flour, rice flour | 0.1–60 g/l |
| Molasses or honey | 0.1 ml/1–100 ml/l |
| Citric acid | 6–600 g/l |
| Water | 3 Liters |
| Vegetable oil | 0.5–300 Liters |

For example, a minimal solution for liquid culture of *L. sulphureus* includes 20 liters of previously boiled water, 40 grams citric acid, and 4 liters safflower oil. The medium is inoculated with *L. sulphureus* mycelial culture. The culture is incubated at room temperature, in stationary phase, under indirect sunlight with a cotton plug to prevent contamination and allow aeration. In a second example of a liquid culture, the components in the undefined media without sterilization. A culture of wine yeast is introduced to the liquid medium and allowed to grow to form in a large yeast culture. A *Laetiporus sulphureous* culture is then added to the culture. This procedure will recognized as being similar to fungal succession in wood decay. Nematicidal activity has been found in the culture fluids.

Metabolic Conversion of Oils to Produce Pesticide and Nematicide Metabolites

In another embodiment, the present invention includes methods for producing pesticidal and nematicidal compositions by culturing fungi on vegetable oil, or by mixing or layering vegetable oil with the above-described liquid defined or undefined media in the amounts shown in Table 4. Mixtures of vegetable oils can also be used. Examples of suitable vegetable oils include, but are not limited to: canola oil, sunflower oil, cottonseed oil, safflower oil, olive oil, corn oil, macadamia nut oil, and soybean oil. Still other suitable oils will be apparent to those of skill in the fungus culture arts. As shown herein, digested vegetable oils provide effective nematicides: exposure of nematodes to compositions comprising *L. sulphureus*-digested safflower and canola oil provided 87% and 85% killing percentages respectively at 1:5,000 dilution, with DAWN® at 1:800.

TABLE 4

| Components for Oil Conversion | Amount |
| --- | --- |
| Clarified culture Fluid | 1.0 ml |
| Vegetable oil(s) | 1.0 Liter |
| Water | 10.0 ml |

In general, suitable vegetable oils include those vegetable oils having the following approximate nutritional content per tablespoon: 120 calories (fat), saturated fat (1 g) polyunsaturated fat (4–12 g), monounsaturated fat (6–12 g), vitamin E (less than about 25% of the Recommended Daily Value for human consumption), and less than about 1% of dietary fiber, sugars, vitamin A, vitamin C, calcium, and iron. As shown herein, the nematicidal effectiveness of the vegetable oil was found to correlate with a Saturation Index defined as follows:

Saturation Index=Percentage of Polyunsaturation/Percentage of Monounsaturation

As shown herein, vegetable oils converted using 4-week-old cultures and having a Saturation Index of less than about 1.0, more specifically less than about 0.5, and, still more specifically, less than about 0.2 are provide useful nematicidal activity. In one embodiment, the saturation index of the vegetable oil is between about 0.1 and about 0.8. In another embodiment, the saturation index of the vegetable oil is between about 0.1 and about 0.6. Specific embodiments include those for which the saturation index is about 0.2 and those for which the saturation index is about 0.6. However, the ability of the culture to digest polyunsaturated oils improves with the age of the culture. Therefore, any correlation between saturation index and activity will depend on the age of the culture. In one embodiment, the culture fluid, water and vegetable oil are placed together in a suitable container and shaken by hand, mechanically blended, or left stationary. During conversion a hazy emulsion will occur. The mixing time, degree of agitation, liquid volume, and temperature will affect conversion. Optimization of these variables can be achieved using methods and materials known in the art. Alternatively, the vegetable oil(s) are layered on the liquid media and a gentle rotation using a rotary shaker is provided under conditions that avoid forming an emulsion. In yet another alternative, the vegetable oil(s) can be mixed vigorously with the liquid media, then shake-incubated at speeds and temperatures that allow phase separation. The oil is then collected.

Production of Nematicidal Compositions

Once the culture medium has been prepared, the fungi are cultured under the appropriate conditions for production of the pesticidal composition of the invention. Generally, if the media described above are used, then culturing can be performed using methods and materials known to those of skill in the art. Examples of culture periods for the growth conditions described above are provided in Table 5 below.

TABLE 5

| Culture Medium | Time |
|---|---|
| Solid | 3 Weeks |
| Liquid | 1–3 Weeks |
| Agar Plates | 1–3 Weeks |
| Converted Oils | 24–36 Hours |

Stationary converted oil with take at least 3 weeks for maximum conversion; incubation time varies with inoculation method. Single point or multiple point inoculation will vary the incubation time. In addition, oils other than vegetable oils can be digested. For example, cultures of *L. sulphureus* comprising 200 ml of 30 W engine oil in 250 ml of liquid culture medium have been maintained for 5 months.

If a solid substrate is used to grow the fungal cultures, then the substrate and fungi are rinsed with water. The water rinse is allowed to stand for a period, and the water collected to provide the pesticide solution. If a liquid culture medium is used under growth conditions that suppress fruiting, then the medium and fungi are separated by filtration and the filtrate is used for pesticide applications. If fruiting is allowed to occur, then a cold shock is applied prior to filtration to improve the pesticidal qualities of the filtrate.

In some cases it is advantageous to use a vegetable oil as described above. A surfactant is often useful to aid dispersion of the pesticide. In addition, penetration of the nematode skin is also aided by a surfactant. Both of these requirements are satisfied by detergents that have an ionic surfactant or a mixture of an ionic and a non-ionic surfactant, including, but not limited to, those substances sold under the tradenames Dawn®, Joy®, Ajax®, LI®700, and PALMOLIVE, in addition to ionic surfactants such as ammonium laureth sulfate, ammonium lauryl sulfate ($NH_4C_{12}H_{25}SO_4$), sodium laryl sulfate ($NaC_{12}H_{25}SO_4$) and sodium dodecyl sulfate ("SDS"). Also, dimethylsulfoxide ("DMSO") has properties consistent with the above-described surfactants with respect to facilitating the transport of bioactive materials across membranes. Other useful surfactants include those preparations sold as shampoos. Most shampoos are based on more ionic than nonionic in formulation in order to remove oil from hair. For example, Prell® shampoo has been found to be a good carrier for the nematicide-containing oils. However, nonionic surfactants, such as most agricultural surfactants, are less effective at carrying the pesticide-containing oil into nematodes.

Control of Nematode Infestation

In one aspect, the present invention provides methods and materials for the prevention, control, and eradication, of nematode infestation and, more particularly, nematode-related damage to plants. An amount of the composition that is effective to cause such prevention, control, and/or eradication will be referred to herein as an "effective amount" or a "nematicidal-effective amount". According to one embodiment of this aspect of the invention, a nematode is contacted with effective amount of a composition of the invention. In another embodiment, the present invention provides a method of preventing nematode-related damage to a plant in which an effective amount of a composition of the invention is administered to the locus, roots, leaves, or seeds of such plant.

Pesticide compositions of the invention can be delivered using known methods and materials. For example, the compositions of the invention can be delivered in the form of liquids, powders, or solids depending on the desired route of administration factors such as soil type, climate, plant species, among other considerations. Delivery can be by spray, using such devices as hand-held spray bottles, pressurized sprayers, spray guns mounted on trucks, and aerial spraying. Powders can be delivered by hand or by dispensers that are pushed or towed. Solid formulations can be delivered by hand or by machine. The liquid, solid, or powder including the composition of the invention can contain additional ingredients such as inert carriers, dilution agents, or other pesticides. Seed treatment, sidebanding, and field injection can also be used to deliver the composition of the invention. Still other delivery methods include overhead irrigation, chisel in with shank, drip system, slow release capsule, slow release gel, fogging, micro encapsulation, spray, and misting. Further examples can be found in the literature known to those skilled in the art. See, e.g., Kloepper, J. W. and Schroth, M. N. "Development of a Powder Formulation of Rhizobacteria for Inoculation of Potato Seed Pieces" 71 *Phytopathology* 590–592 (1981); and Vidhyasekaran, P. and Muthamilan, M.,. "Development of Formulations of *Pseudomonas Fluorescens* for Control of Chickpea Wilt", 79 *Plant Dis.* 782–786 (1995). The determination of the amount of composition of the invention to use, the form and method of delivery, and use of additional pesticide can be made by one of skill in the agriculture arts. For example, plants can be grown in the greenhouse in soil infested with the appropriate nematode. Various dilutions and other formulations of the pesticide composition of the invention prepared in accordance with the description herein, optionally including a surfactant as described above, are added to achieve 1 to 6 acre/inch equivalent of liquid.

Replicated pots are analyzed for disease, nematode population, and plant performance. Split root trials also are performed to determine if there is translocation of the nematicidal material through the plant. Such, tests can determine the stability of the pesticide composition of the invention when it is introduced into the soil.

Field trials can be performed as described in the following example. Dilutions of the composition of the invention are applied to pineapple and potato field soil containing nematodes. The nematodes are extracted over time, e.g., by wet sieving, and nematode mortality is determined and recorded. To determine the pesticide's effect on plants, extracts are concentrated and plant roots dipped in 100×, 50×, 10×, and 1× concentrates. The plants are removed, potted and evaluated for growth effects by recording plant height, root length, and total wet weight. To determine whether the pesticide can be translocated by the plant, a split root test can be performed using ex-plant potato plants.

In addition, known concentrations of the composition of the invention can be incorporated into soil collected from pineapple and potato fields. Water extracts (or phosphate buffer extracts) are collected at 2-day intervals, filter sterilized (e.g., using a 0.2 μm filter) and assayed for nematicidal activity. If activity can be detected, small field plots will be planted in different geographical locations to determine field effectiveness against nematodes. In these tests, nematodes are collected, identified, and enumerated prior to planting of the crop. The nematicidal composition (as an aqueous solution) is added to soak at least the top six inches of soil. The material is applied one to four times during the growing season at four different rates. In another series of tests, plant roots are dipped in a solution of the nematicidal compound and planted in field soil infested with plant parasitic nematodes. Again, populations will be determined prior to planting. In both experiments, nematode populations will be determined at two-month intervals. Plants will be examined for root disease at each nematode sampling period and at the end of the experiment. At the end of the growing season, disease severity will be recorded on a scale using, for example, a score of 0 to 5 where a score of 0 indicates no observable disease and a score of 5 indicates severe disease. The plots will be harvested and yields determined. All results will be statistically analyzed using known techniques such as Tukey's Honestly Significant Difference (HSD) test.

Identification and Preparation of Nematicidal Compounds and Compositions

In another aspect, the pesticide, and, more particularly, nematicide, composition provided by the present invention can be used to derive specific chemical compounds having desirable pesticide and nematicide qualities. Such compounds can form the basis of synthetic derivatives having still more desirable pesticide and nematicide properties. In still another aspect, the methods and compositions described herein can also be used to identify specific genes for producing pesticide and nematicide compounds. Such genes can be modified or transfected into different hosts to provide more efficient production of the compounds and compositions of the invention, as well as transgenic plants that are resistant to pesticide, and, more particularly, nematode, infestation as well as rhizoplane bacteria that express the pesticide. Such chemical and genetic embodiments can be accomplished by the application of methods familiar to those of skill in the agricultural chemistry and genetics arts using the methods, materials, and compositions provided by the present invention.

Chemical Analysis and Development

An example of the elucidation of the chemical composition of the composition of the invention is provided herein. Initial experiments to determine tolerance of the active principle to desiccation are performed by first drying the culture medium. Extractions from the dried media are then be performed with water. The extracts are incubated at different temperatures to determine heat tolerance. Preliminary size estimation is performed, e.g., by ultrafiltration through membrane sieves of varying molecular weight cut-offs. Data from these tests will provide sufficient information to generate basic handling guidelines for use of this material in subsequent tests. Standard methods in solvent extraction/partitioning, chromatography and physical tests are used to extract and characterize the compounds from the different fungal genera.

Purification of active chemical compounds from the water extracts can be performed using the guidelines described by Shimizu. 48 *J. Natural Products* 223–235 (1985). Standard methods of solvent partitioning, followed by gel filtration, and ion-exchange chromatography, can be used to obtain at least partial purification of the active compounds. Solvent partitioning into polar and non-polar components can provide basic information on the nature of the compound. For example, extraction into chloroform would suggest that the molecule is a lipid or has a lipid moiety. Extraction into non-polar solvents such as ethyl acetate after varying the sample pH may suggest the molecule is a protein or peptide-like. Qualitative tests (e.g., the ninhydrin test for amines, the anthrone test for carbohydrates, or selected stains for peptide/protein composition) can also be used to identify the chemical nature of the active material and facilitate further purification.

If the bioactive fractions are macromolecules, standard biochemical techniques can be employed for purification and characterization. Examples include electrophoretic methods such as isoelectric focusing and polyacrylamide gel electrophoresis. Confirmation of the peptide nature of the active fractions can be made by using various standard treatments such as proteases (for proteins/peptides), ConA (for certain sugar dimers and associated glycoproteins), periodic acid (carbohydrates), nucleases (nucleic acids), and the like.

For molecules with low molecular weights, the active fractions can be separated by using SP- and QAE-Sephadex columns into neutral and strongly cationic and anionic components. Based on these data, ion exchange can used to purify the material further. The active compound(s) will then be subjected to high-pressure liquid chromatography-mass spectral (HPLC-MS) analysis to provide a tentative structural identification of the active principle. Magnetic resonance (MR) studies such as proton and carbon-13 nuclear magnetic resonance ($^1$HNMR and $^{13}$CNMR), in single and multiple dimensions, can be used in conjunction with infrared (IR) techniques for more detailed structural analysis. These studies can provide a chemical structural description of the active compound(s). Final structural confirmation(s) can be determined by chemical synthesis and HPLC-MS comparison with the natural products.

Knowledge of the structure of the active compounds can be used to derive new compounds having specific, desired characteristics. Such derived compounds can be made using methods and materials known in the chemistry arts. Examples of such methods include the use of qualitative structure-activity relationship ("QSAR") analysis to determine structural and electronic features relevant to the biological activity of the isolated compound(s). Structural analysis can also be performed using a variety of computer techniques to determine other molecular features such as molecule shape, volume, pH, and the like, and correlate such features to the biological activity of the active compound(s). Computer analysis can also be used to search chemical databases for other molecule having similar structural features. Compounds found by such searching can be tested for activity as described herein. New active compounds can be obtained by known chemical synthetic methods, for example by the preparation and screening of combinatorial libraries of compounds.

Molecular Genetic Analysis

Biologically active metabolites are often produced by unique structural and regulatory DNA sequences. The strategies used for isolation and characterization of these sequences are dependent on the nature of the metabolite of interest. Thus, selection of approaches used to elucidate the genetics of pesticide product(s) by fungi such as *G. lucidium, L. edodes, P. ostreatus,* and *P. sajor-caju* will be influenced by the results of the biochemical characterization of the composition and its active components as described in 0 above.

If the characterization of the active component indicates that it is a peptide or protein, gene isolation and identification can be performed by construction of copy DNA (cDNA) libraries from isolated fungal mRNA. For example, mRNA can be cold-collected from cultures grown under defined conditions. A DNA template (cDNA) can be synthesized from the collected mRNA using a suitable reverse transcriptase. Complementary DNA strand synthesis can then be produced using the cDNA segments as templates, random primers, and DNA polymerase. The double-stranded derivatives can then be ligated into broad host-range plasmids (shuttle vectors) suitable for transformation of *E. coli,* Bacillus spp., yeast, and the like, using known methods and materials. The transformed hosts can be screened for extracellular or intracellular expression of pesticide activity. Alternatively, in vitro expression systems, such as wheat germ extract and rabbit reticulocyte expression systems, can be used to identify putative active component genes.

If the active component is a peptide, the amino acid sequence of the peptide can be determined using standard procedures as described above. Sequence confirmation can be followed by in vitro synthesis and nematode sensitivity tests. Degenerate DNA probes can be synthesized based on the derived amino acid structure. PCR amplification using the DNA probes as primer templates on total genomic DNA, followed by cloning into appropriate vectors, can then be performed to identify the gene. Alternatively, the DNA can be used as probes to identify homologous sequences in a genomic library.

If the active component is not proteinaceous in nature, or the final peptide/protein is a processed molecule, a standard cosmid library can be constructed for each of the fungal isolates in cosmid vectors. Non-specific mutations can be induced in the fungi, e.g., by treating basidiospores with chemical mutagens such as ethylmethane sulfate, nitrosoguanadine, and acridine orange. Alternatively, exposure of basidiospores to UV light may also be used to generate mutants. Conditions that ensure that a mutational event has occurred (i.e., treatment that results in 99% mortality of treated spores) can be determined using known methods. Cultures derived from single spore separation will be screened for loss of the nematicidal activity. Molecular techniques such as gene cloning, transformation, and the like have been developed for several other basidiomycetes. These techniques can be used to transform protoplasts of the pesticidally inactive "tox" mutants with individual clones from the cosmid library. Culture supernatants and cell lysates of the bacterial cosmid clones, and fungal transformants can be screened for toxin production with axenic nematode cultures. Through this process, the complete set of genes needed for production of the nematicidal compound can be determined. This information could then be used to develop molecular probes for identification of similar systems in other basidiomycetes. Ultimately, these genes would serve as the reporter sequences that can be used to identify positive and negative regulatory elements in the fungal antagonist. Thus, the genetic information could be used to enhance or control production of the nematicidal compound.

EXAMPLES

The following examples describe specific aspects of the invention to illustrate the invention and aid those of skill in the art in understanding and practicing the invention. However, these examples should not be construed as limiting the invention in any manner. The procedures described in the examples set forth below can be performed using methods and materials commonly known among those skilled in the art of culturing fungi, unless otherwise noted.

Preparation of Growth Media

The present invention provides compositions having useful pesticidal, and, more particularly, nematicidal properties by culturing fungi using growth media and/or culturing conditions that inhibit fruiting of the fungi. Several examples of growth media effective to induce the production of compositions having nematicidal (as well as pesticidal) properties are described in this Section 0.

Growth Medium 1

The following substances were combined in the amounts shown in Table 6:

TABLE 6

| | |
|---|---|
| Glucose | 30.0 g/l; |
| $K_2HPO_4$ | 1.0 g/l; |
| Yeast extract | 4.0 g/l; |
| Nutrient Solution | 10 ml (added after autoclaving) |

The nutrient solution was prepared by combining the substances listed below in the amounts indicated in Table 7:

TABLE 7

| | |
|---|---|
| $(NH_4)_2SO_4$ | 3 g/100 ml; |
| $MgSO_4.7H_2O$ | 5 g/100 ml; |
| KCl | 5 g/100 ml; |
| $MnSO_4$ | 0.02 g/100 ml; |
| $FeSO_4$ | 0.02 g/100 ml; |
| $ZnSO_4.7H_2O$ | 0.02 g/100 ml; and |
| Thiamine | 0.001 g/100 ml. |

Growth Medium 2

The following substances were combined in the amounts shown in Table 8 to prepare a second growth medium:

TABLE 8

| | |
|---|---|
| Ground oatmeal | 15 g/l |
| Brewer's yeast | 15 g/l |
| Corn gluten | 15 g/l |
| Molasses | 1 tsp./l |
| Citric acid | 2 g/l |
| Water | 1 L |
| Vegetable oil | 2 ml/l |

The substances were combined and about 500 ml of the mixture was autoclaved for about 40 minutes in a 2-liter flask. One hundred milligrams of tetracycline or streptomycin was added if the medium was for isolation.

Growth Medium 3

A third growth medium was provided using the materials and amounts shown in Table 9 Tetracycline (100 mg) and Streptomycin 100 mg are added for isolation from mushroom material.

TABLE 9

| | |
|---|---|
| Infusion from potatoes | 200 g/l (or 4 g/l of potato extract) |
| Bacto-Malt Extract | 20 g/l (or 30 g/l malt extract agar) |
| Sucrose | 60 g/l |
| Yeast Extract | 3 g/l |
| Bacto-Peptone | 1 g/l |
| Molasses | 1 teaspoon/l |
| Ground Quaker Oats | 1 tablespoon/l |
| Bacto-Agar | 25 g/l (or 15 g/l if malt extract agar is used) |
| Water | 1 L |

Solid Growth Medium

The following is an example of the use of a solid growth substrate to culture a fungus of the species *Ganoderma lucidium* under conditions effective for the fungus to produce a metabolite having nematicidal activity. A grain block was prepared as follows. The following ingredients were obtained in the quantities indicated:

| | |
|---|---|
| Russet Potatoes | 10 lb. |
| Rolled Barley Grain | 5 lb. |
| Whole Sorghum grain | 200 lb. |
| Whole Oat grain | 35 lb. |
| Maple pea sprouts | 5 lb. |
| Brewer's yeast Powder | 6 lb. |
| Hulled sunflower seeds | 2 lb. |
| Soybean meal | 1.5 lb. |
| Corn gluten meal | 1.5 lb. |
| Whole garlic | 1.5 lb. |
| Sunflower oil | 10 Tbsp. |
| Wheat germ oil | 10 Tbsp. |
| Molasses | 4 Tbsp. |
| Water | 25 Gal. |
| Milk | 0.25 Gal. |
| Limestone powder | 30 lb. |
| Gypsum powder | 160 lb. |
| Cottonseed meal | 40 lb. |

The water, potatoes, milk, garlic, sunflower, yeast, and soybean were boiled and mixed until small pieces formed. The maple pea sprouts were added and cooked until soft, after which the oats and sorghum were added along with additional water to cover the grain. The mixture was cooked until the water level was 3–4 inches below the grain level, and then the heat was removed. The grain was half-cooked and semi-hard. This was allowed to cool for about 24 hours. After cooling the grain was removed and mixed with the limestone, gypsum, and cottonseed until coated and there was no significant clumping. The coated material was formed into blocks and packed into bags.

One block was selected for inoculation. The block was inoculated with *Ganoderma lucidium*, and incubated in the dark for about 3 months at room temperature. The block was removed to a lighted room where fruiting occurred within the bag. About 30 ml of sterile water was injected into the bag and allowed to accumulate and rest at the bottom of the bag for about 4 hours. The water obtained a slight brown color during this period.

A 3 mm aliquot of the water was withdrawn from the bag and placed onto a clean petri dish. Five saprophytic nematodes of Rhabditus spp. were placed in the water and observed. Within about 30 seconds of exposure, the nematodes showed reduced motility, and, after about 60 seconds all nematode motion ceased among the smaller nematodes. Removal of these nematodes to fresh water did not produce any renewed movement. After about 3 minutes, the larger nematodes ceased movement. These too did not revive when placed in fresh water.

In a separate experiment, a small, segmented worm was exposed to the water extract. The worm also ceased motion prior to the small and large nematodes. Thus, the *G. lucidium* extract obtained as described herein showed both nematicidal as well as more general pesticidal capability.

In another experiment, ten mosquito larvae were placed in a 5 ml solution. The solution consisted of *G. tsugae* digested safflower oil at 1:500 with Dawn® detergent at 1:1000. The test was conducted at room temperature. In 4 days, 80% of the larvae died.

Preparation of Compositions Having Nematicidal Activity

Preparation From Solid Substrates

Seven solid grain blocks, each approximately 10 pounds (lbs), were produced using the methods and materials described herein above. Cultures of *Pleurotus ostreatus, Lentinus edodes, Pleurotus sajor-caju,* Morchella, *Ganoderma lucidium, Ganoderma tsugae,* and *Laetiporeus sulphurus* were grown using the blocks, one culture for each block. After about 4 weeks of incubation at room temperature in the dark, each of the blocks was placed in approximately 12 liters of water. Water samples were taken after 1 week of soaking and the nematicidal activity of the samples was tested at 1:50, 1:100, 1:400 and 1:1,000 dilutions. The fungal extract was diluted with a water solution of Dawn® at 1:1,000. All species showed some nematicidal activity against rootknot larvae.

Preparation from Liquid Media

Liquid culture media was prepared as described herein. Agar plates were inoculated with *Pleurotus ostreatus, Pleurotus saju-caju, Flammulina velutipes,* Morchella spp., *Lentinus edodes, Ganoderma lucidium, Ganoderma tsugae,* and *Laetiporus sulphureus*. Cultures were incubated at room temperature with a 12-hour day. Plates were grown for 30 days and then scraped. One-half gram (0.5 g) of the scrapings was added to 100 ml of water and then macerated. The material was filtered through Whatman #1 filter paper. The resulting fungal extract was diluted with a Dawn® solution consisting of 1:1,000 Dawn® to water. Dilution levels of 1:50, 1:100, 1:400 were used against rootknot larvae. Nematicidal activity was found in all preparations, with *Laetiporus sulphureus, Ganoderma tsugae, Ganoderma lucidium, Pleurotus sajor-caju,* and *Pleurotus ostreatus* showing greater activity than *Lentinus edodes* and Morchella spp.

Preparation from Oil Conversion

Agar plates were prepared according to Growth Medium 3 using *Pleurotus ostreatus, Pleurotus sajor-caju, Ganoderma tsugae, Ganoderma lucidium* and *Laetiporus sulphureus*. After 21 days of incubation at room temperature in 12 hour days and indirect sunlight, the liquid cultures ("LCs") were sampled. The LCs were diluted with water containing 1:1,000 Dawn® detergent and tested against rootknot nematode larvae. Nematocidal activity was present in all liquid cultures. However when a *Laetiporus sulphureus* liquid culture was kept in a refrigerator for 30 days, the observed nematocidal activity increased substantially from a 1:100 dilution to a 1:800 dilution. This temperature effect was not observed in the Ganoderma or Pleurotus species. The nematocidal activity of the aqueous phase of the liquid medium was lost if the fungal extract was frozen then thawed, the fungal extract dilutions were made, or if the fungal extract was still cold. Upon investigation, the activity was found to be confined to an oily film that appeared on the walls of the container after prolonged exposure to refrigerator temperatures. Nematicidal activity was returned to the liquid medium by adding a drop of Dawn® detergent to the fungal extract.

Alternatively, the mycelial mass was filtered from the culture and 1 ml of culture filtrate was mixed with 10 ml of water and 1 liter of vegetable oil. Tests for nematicidal activity of the oil. Oil that was mixed for at least about 36 hours developed nematicidal properties. The degree of activity increased with greater mixing periods, and varied among different oils and combinations of oils. See Table 13. The rate of conversion was found to be proportional to the amount of filtrate.

In one experiment, the nutrients in Table 8 were combined together. About 500 ml of the liquid culture was put into a 2,000 ml Erlenmeyer flask and plugged with a cotton stopper. The material was autoclaved for 40 minutes at 121° C. at 15 psi. After cooling to room temperature, the liquid culture inoculated aseptically with 5 agar plugs. The agar plugs had been removed from a colonized agar plate of *L. sullphureus,* and were approximately 0.25 cm in diameter. The agar plates were made using the materials and quantities shown in Table 9. The inoculation was done in a laminar flow hood to maintain sterility.

The inoculated flasks were incubated at room temperature in the dark for about 3 weeks. The flasks remained stationary during that period. After the incubation period, 500 ml of additional oil was added to the flasks. The flasks were placed in indirect sunlight and kept at room temperature. The flasks usually contained a large mycelial mass floating in the liquid culture. If the cultures are not being swirled, the mycelial mass was observed to enter into the oil layer and even grow on top of the oil layer itself.

During the oil addition phase, sterility is broken since the vegetable oil had not been sterilized before adding to the liquid cultures. Usually 500 mls of oil was added to the liquid culture. The flask were placed on a rotary shaker and gently swirled. After 3 weeks, the oil over the *L. sulphureus* became golden in color. Oils digested by the Ganoderma spp. and the Pleurotus spp. however were observed to turn colorless. Oils that changed color were subsequently found to have nematicidal activity. The oil layer was removed and fresh oil was placed over the culture. This relayering of oil on the culture medium was done repeatedly without loss of nematicidal activity.

In another experiment, a liquid culture of *L. sulphureus* was grown with canola oil for 4 weeks. IT was noted that the culture filtrate would digest monounsaturated oils, but not polyunsaturated oils like sunflower oil, as indicated by the formation of an emulsion or haziness of the oil. (More haziness was indicative of more activity in the oil.) Without wishing to be bound by theory, it is possible that lipase activity in the fungi takes place at the water oil interface. Less lipase activity would be consistent with less emulsion formation and, thus, less haziness of the oil.

However, when a liquid culture of *L. sulphuerus* was grown with canola oil for 16 weeks the culture filtrate will digested not only monounsaturated oils, like safflower and canola oils, but also sunflower oil which is a polyunsaturated oil. Again not wishing to be bound by any particular theory of action, this observation is similar to other observations in which a fungus can digest a mixture of sugars only having previously digested simple sugars first. This may indicate that nutrient-induced metabolic changes occur in the fungi.

Nematicidal Activity of the Compositions of the Invention
Nematicidal Activity of Growth Medium 1

In a first experiment, Lentinus and Pleurotus fungal cultures were grown for 7 days using Growth Medium 1. A 200 µl aliquot containing Aphelenchoides spp., Xiphinema spp., Trichodorus spp., and Meloidogyne spp. (larvae) nematodes was placed about 10 mm from the fugal cultures. Within about 24 hours only about 10% of the nematodes placed near the Lentinus culture were motile, while none of the nematodes placed near the Pleurotus culture showed motility. As a control, an aliquot of the nematodes was placed near the medium alone. About 30% of the control group showed motility at the 24-hour mark. Nematodes that appeared to be dead were removed from proximity of the cultures to sterile water and observed for an additional 24 hours. No recovery of motility or other sign of life was observed.

In a second experiment, fungal cultures were grown on Growth Medium 1 for 7 days. A 500 microliter (µl) aliquot of sterile water was placed about 10 millimeters (mm) from the leading edge of the colony and allowed to stand for about 10–15 minutes. The water was collected and placed in 11 small watch glasses. One Rhabditus spp. nematode was placed in each of the watch glasses. The activity of the nematodes was observed over a 24-hour period. The degree of nematode survival over time, expressed as a percentage, is provided in Table 10 below. The results shown are an average of three experiments.

TABLE 10

| Fungal strain\Time | 5 m | 15 m | 30 m | 1 h | 2 h | 3 h | 24 h |
|---|---|---|---|---|---|---|---|
| *Lentinus edodes* | 90 | 51 | 48 | 48 | 45 | 21 | 12 |
| *Pleurotus ostreatus* | 57 | 42 | 40 | 29 | 20 | 18 | 0 |
| *Pleurotus sajor-caju* | 97 | 97 | 50 | 30 | 27 | 14 | 0 |
| Media alone | 100 | 94 | 92 | 92 | 86 | 86 | 33 |

To control for any nematicidal effects of the growth medium, *Pleurotus ostreatus* was cultured in Growth Medium 1 for 7 days. An aliquot of the culture was transferred to water agar and cultured for another 7 days. An aliquot of about 200 µl of water was placed about 10 mm from the water agar culture. Ten Rhabditus spp. nematodes were place in the droplet and observed for a period of about 31 hours. The results of three such experiments confirmed that, on average, only 7 percent of the nematodes survived as long as 31 hours in the presence of the conditioned water as to 85 percent of the nematodes exposed to a control comprising water agar.

Nematicidal Activity from Fruiting Fungi

Culture of fungi from the species: *Flammulina velutipes, Pleurotus ostreatus,* Morchella spp., *Ganoderma lucidium, Ganoderma tsugae,* Auricularia spp., Hypsizgus spp., Agaricus spp., *Laetiporus sulphureus* were obtained as described in Table 11 and grown in the above-described undefined medium. Ten grams of mushroom body were macerated in 100 ml of deionized water for 5 minutes using a blender. The solution was filtered and a dilution series was prepared to determine nematocidial effects of the resulting filtrate.

TABLE 11

| Mushroom Fruiting Body | Source |
|---|---|
| *Flammulina velutipes* | Market |
| *Pleurotus ostreatus* | Grown on cellulose blocks |

TABLE 11-continued

| Mushroom Fruiting Body | Source |
| --- | --- |
| Morchella sp. | Market |
| Ganoderma lucidium | Grown on grain blocks |
| Ganoderma tsugae | Grown on grain blocks |
| Hypsizgus sp. | Market |
| Auricularia sp. | Field collected |
| Agaricus sp. | Market |
| Laetiporus sulphureus | Field collected |

In addition, a liquid culture of *L. sulphureus* was grown for 60 days at room temperature using Growth Medium 2. The culture was then placed in a refrigerator for 30 days at 38° F. to "cold-shock" the culture. The resulting cold-shocked liquid culture was filtered and the filtrate tested for nematicidal activity. A converted oil was also prepared for study by placing 500 ml of safflower oil over a 1-liter culture *Laetiporus sulphureus* for about 21 days.

Rootknot larvae were used as the test organism. The larvae were obtained by harvesting rootknots from infected plant roots. The rootknots were teased open and placed in aerated water. In 2 to 4 days larvae will have emerged from the eggs. Larvae are removed and placed in the appropriate dilution. Exposure to the dilutions varied from 24 to 72 hours followed by a 24-hour clean water rinse. Nematodes were rated as being Alive or Dead at specific dilutions. The effectiveness of the nematicidal effects of the filtrate was expressed as the percent of nematodes determined to have died during the exposure period (Table 12).

TABLE 12

| Treatment | Dilution | Effectiveness |
| --- | --- | --- |
| Water (Control) | N/A | 18% |
| Flammulina velutipes | 1:500 | 47% |
| Pleurotus ostreatus | 1:500 | 73% |
| Morchella spp. | 1:500 | 64% |
| Ganoderma lucidium | 1:500 | 77% |
| Ganoderma tsugae | 1:500 | 73% |
| Auricularia spp. | 1:500 | 23% |
| Hypsizgus spp. | 1:500 | 50% |
| Agaricus spp. | 1:500 | 26% |
| Laetiporus sulphureus | 1:500 | 40% |
| L. sulphureus (cold treated liquid culture) | 1:3,000 | 81% |
| Safflower Oil digested by L. sulphureus liquid culture | 1:5,000 | 95% |

Nematicidal Activity from Digested Vegetable Oils

Five hundred milliliters (ml) of safflower, canola, corn, cottonseed, and soybean oils were added one oil to each of five, one-liter liquid cultures of *L. sulphureus*. The mixtures were incubated at room temperature for 4 weeks. The digested vegetable oil was extracted and diluted to 1:5,000. The dilution was combined with a 1:800 Dawn® detergent-:water solution. Sample populations of rootknot larvae were exposed to the diluted composition and the effectiveness of the composition, expressed as the percentage of larvae killed, was determined. Undigested safflower oil was used as a control. The results are shown in Table 13.

TABLE 13

| Oil | Saturation Index | Effectiveness |
| --- | --- | --- |
| Safflower | 0.19 | 87% |
| Canola | 0.6 | 85% |
| Cottonseed | 2.9 | 77% |
| Soybean | 2.5 | 70% |
| Safflower/Corn Oil (50:50)[2] | 0.73 | 97% |
| Sunflower[1] | 2.8 | 90% |
| Corn | 2.4 | 50% |
| Control | N/A | 15% |

[1]Derived from a 16-week-old culture. Kill time took about 4 days.
[2]Derived from a 16-week-old culture.

The nematicidal effectiveness of the oil was found to correlate with a saturation index defined to be the ratio of the percentage of polyunsaturation of the oil to the percentage of monounsaturation of the oil. Thus, oils having a lower saturation index are more effective than oils having a higher saturation index. However, as incubation time increased, the ability of the culture to digest polyunsaturated oils was found to increase as well. Thus, Table 13 is representative only of the nematicidal properties of the converted oil at the incubation time indicated.

Nematicidal Activity in Soil
Nematicidal Activity Against Adult Nematodes

A field trial of the composition of the invention was performed in pineapple field soil containing plants against reniform nematodes. In the trial, a single application of a 1:5,000 dilution (w/Dawn® detergent at 1:800) of Laetiporus-treated safflower oil was applied to the soil (until the uppermost 6 inches of the soil were drenched) and the resulting nematode populations monitored over time for three replicate tests (live counts). The results of an average of the test results is shown in FIG. 1. At seven days, a 77% reduction was observed compared to controls. At 18 days, populations in the treated soil were 9% of those in the controls. Populations recovered slightly at 60 days. The increase in populations over time was due to new larvae hatching from eggs. This observation indicates that residual soil activity decreases over time. This would minimize resistance developing in nematode populations and suggests that water quality contamination would be minimal. Thus, the results demonstrate soil treatment to be effective in reducing infestation and provide adequate protection for plant establishment.

In pot trials, root mass was found to have doubled in tomato plants challenged with root knot larvae when treated and no galls were observed. Growth of papaya and squash plants noticeably improved with one soil application. Thus, the nematicidal composition appears to be useful on a wide variety of plants.

Comparison of Nematicidal Activity Against a Commercial Nematicide

A trial comparing various embodiments of the nematicidal composition of the present invention and the commercially available nematicide NEMACUR® 3 (ethyl 3-methyl-4-(methylthio)phenyl(1-methylethyl)phosphoramidate, available commercially from Bayer, Vero Beach, Fla.) against root-knot nematode was performed as follows.

Treatments including *Laetiporus sulphureus*-digested safflower, olive, macadamia, and canola oils, in addition to canola oil submerged on *L. sulphureus,* sunflower oil combined with *L. sulphureus* 534, and sunflower and soybean oils combined with *L. sulphureus* 523, were prepared as described above. The treatments were tank-mixed with a liquid detergent (DAWN®) at 0.125%. NEMACUR® and DAWN® were used as standards. Each treatment was applied to 6 tomato plants, each planted in a pot containing 1,000 grams (g) of soil infested with root-knot nematode (*Meloidogyne incongnita*). The plants were examined for height, root length, root damage, and overall appearance after about 5–6 weeks.

The results demonstrated the nematicidal preparations made from safflower oil digested by *L. sulphureus* 534 and canola oil digested by *L. sulphureus* 534 provided protection nearly identical to NEMACUR® 3. Thus, the nematicide of the present invention was found to have nematicide effectiveness nearly identical to that of the commercially-available nematicide.

Nematicidal Against Adult Nematodes and Nematode Eggs

The utility of the nematicidal composition of the invention against nematode eggs was also tested. A bioassay unit was by suspending a 36 μm-pore nylon mesh (available commercially as NITEX 7-30/20) between two 50 cubic centimeter (cc) Tri-Pour disposable plastic beakers (purchased from Sherwood Medical Industries, St. Louis, Mo.). The beakers were modified by cutting off the portion of the beaker between the 20 cc and 25 cc markings for the top or the 35 cc to 40 cc marks for the bottom, and the mesh and beakers washed with SPARKLEEN. Each unit was set in a 80×15 mm$^2$ petri dish bottom and autoclaved prior to use. New bioassay units were constructed for each experiment.

Treatments were prepared by growing liquid culture of *Ganoderma lucidium* in Growth Medium 2 as described above. The nematicidal composition was obtained as described above and applied to the soil as 1:10, 1:100, 1:1000, and 1:10,000-fold aqueous dilutions (shown as Treatments C–G respectively in FIGS. 2 and 3). Water and 30 mM zinc sulfate (ZnSO$_4$) were also used as controls (shown as Treatments A and B respectively in FIGS. 2 and 3). *Heterodera glycines* egg and second juvenile ("J2") populations were determined by pipetting several aliquots into a petri dish and counting the eggs and nematodes under a microscope. The *H. glycines* egg suspensions were maintained by bubbling air into the suspension. The air was supplied by an aquarium pump that pumped the air through rubber tubing and an autoclaved pipette with a cotton plug. The mesh was kept in contact with the Treatment solution between counts during the experiments. The bioassay units were stored between counts in dessicators on porcelain or plastic places suspended above distilled water to maintain humidity and liquid levels that were maintained at a temperature of 20° C.

To perform the bioassays, 9 cc of each Treatment, plus *H. glycines* egg suspensions and autoclaved distilled water were combined to make a 10 cc solution that was pipetteted onto the mesh in the petri dishes. Emerged J2 that passed through the mesh were counted aseptically in a hood in which the mesh and cut-off beakers were supported on a ring stand using a dissecting microscope. The petri dish bottoms were arranged with corresponding petri dish tops that had been demarcated with counting lines. J2 counts were performed every 3 days over a 12-day period. The percentage of emerging J2 were determined as an indicator of nematicidal effectiveness.

Figure 2:
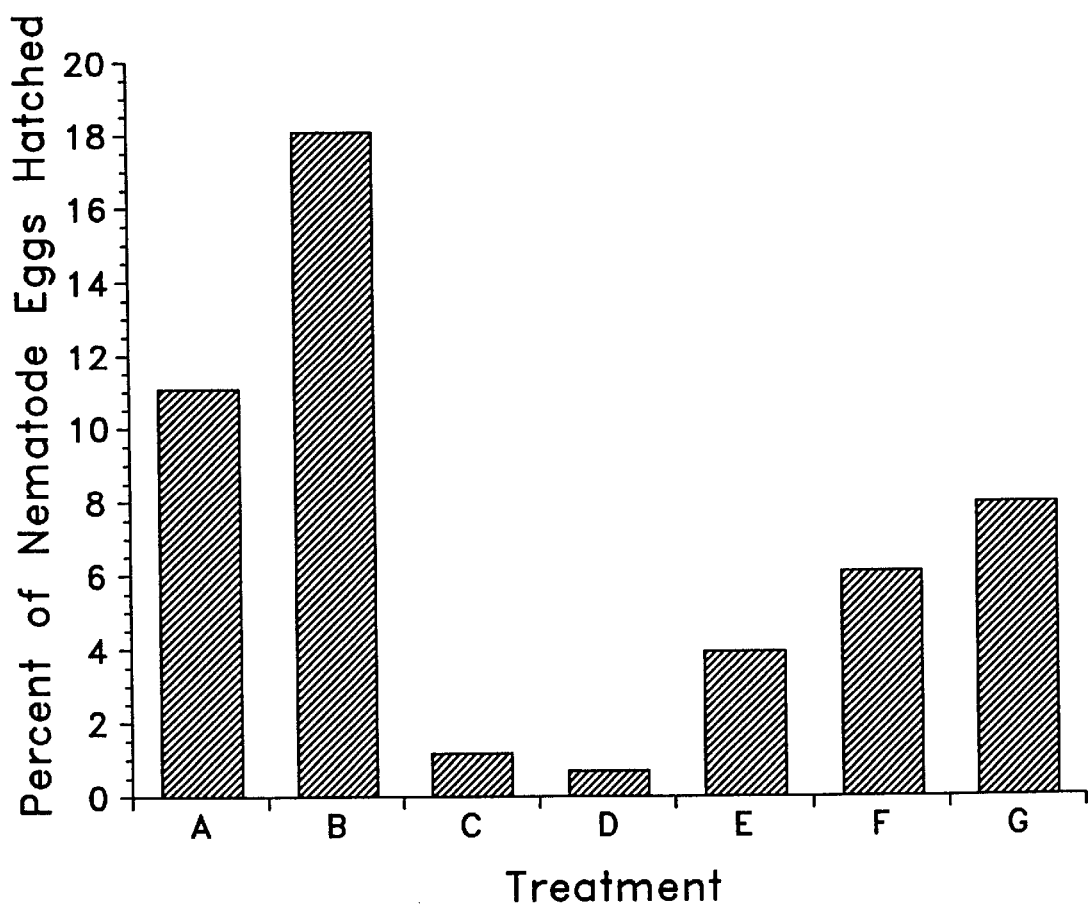
FIG. 2 is a column chart showing the effectiveness of nematicidal compositions prepared from Ganoderma mushrooms at no dilution ("C"), and 10-fold serial dilutions of 1:10–1:10,000 ("D"–"G") compared to water ("A") and $ZnSO_4$ ("B") against soybean cyst nematode eggs.
Figure 3:
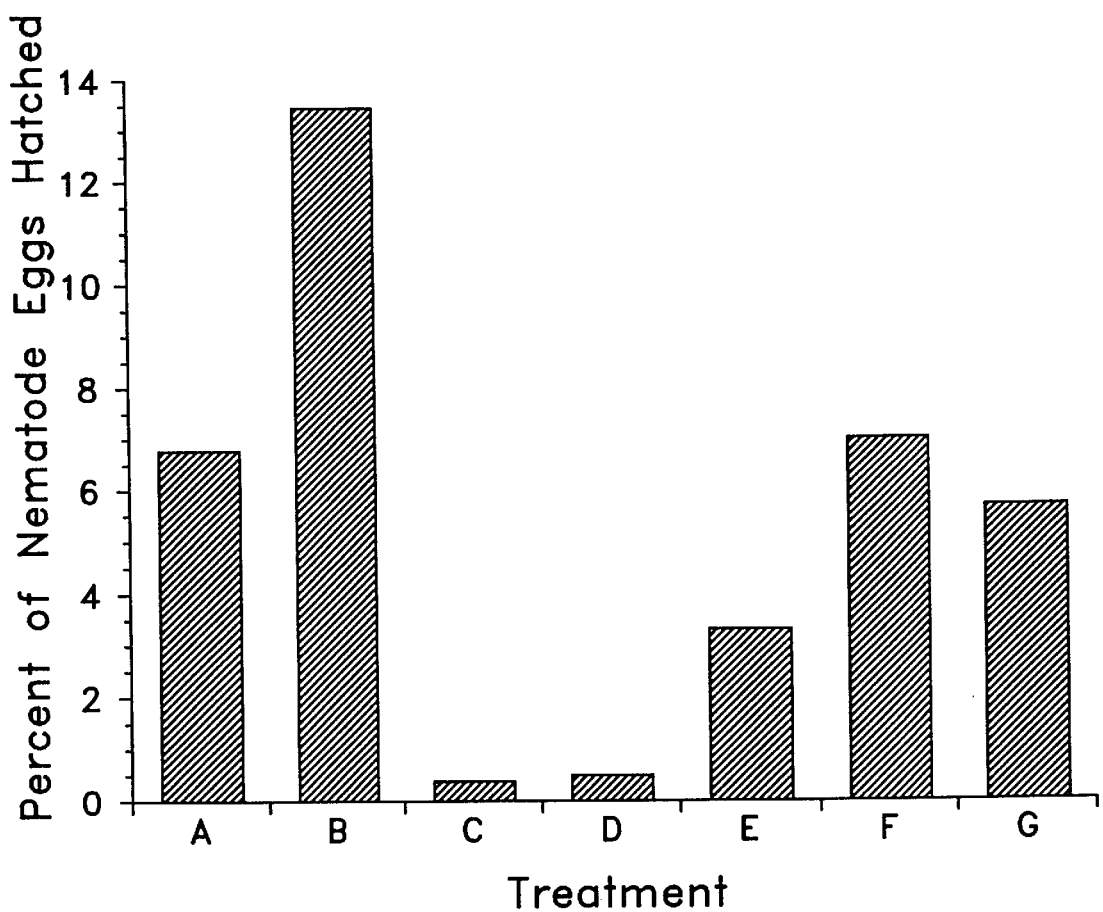
FIG. 3 is a column chart showing the effectiveness of nematicidal compositions prepared from Ganoderma mushrooms at no dilution ("C"), and 10-fold serial dilutions of 1:10–1:10,000 ("D"–"G") compared to water ("A") and $ZnSO_4$ ("B") against soybean cyst nematode eggs.

FIGS. 2 and 3 show the results of two such experiments. These results demonstrate that undiluted and 1:10 dilutions of the nematicidal composition of the invention has exceptionally strong nematicidal effects on *H. glycines* eggs. As shown in FIG. 2, only 1.2% and 0.7% of the eggs hatching under neat and 1:10 dilutions respectively. The results shown in FIG. 3 were better still, indicating that neat and 1:10 dilutions prevented 99.6% and 99.4% of the eggs from hatching.

Conclusion

Thus, from the foregoing it will be seen that the present invention provides important new pesticide compositions and methods. More particularly, the present invention provides a highly effective nematicide that is derived from natural sources and appears to be biodegradable. The methods and materials provided by the invention can therefore be used to eliminate or prevent nematode infestation, treat nematode infection, and serve as a basis for developing still more sophisticated nematicidal compositions.

Although certain embodiments and examples have been used to describe the present invention, it will be apparent to those having skill in the art that various changes can be made to those embodiment and/or examples without departing from the scope or spirit of the present invention. For example, it will be appreciated from the foregoing that various fungi from the basidiomycetes and ascomycetes in addition those specific species described herein can be cultured under the conditions described herein to produce pesticide compositions. Culture conditions that suppress fruiting can be established using temperature and/or lighting and/or nutrient conditions other than those exemplified herein. Furthermore, the compounds and compositions described herein may have application in the medical arts to treat and/or prevent nematode infection in humans and animals. Thus, various fugal species grown using the materials and conditions described herein could be used at therapeutic agents by incorporation into the diet or by extraction of biologically active components as described hereinabove.

What is claimed is:

1. A method for reducing nematode infestation in a plant, comprising the step of administering to said plant which is infested with nematodes a nematicidal amount of a composition which comprises a mixture of a) a nematocidal product of treatment of at least one vegetable oil by a culture of, or by a filtrate from a culture of, basidiomycete or ascomycete fungi, wherein said treatment comprises mixing said oil and said culture or filtrate followed by recovering said treated oil to provide for said nematocidal product of treatment and b) an aqueous solution of a surfactant, whereby said nematode infestation is reduced.

2. The method of claim 1 wherein said fungus is of the genus Ganoderma, Laetiporus, Lentinus, Morchella, or Pluerotus.

3. The method of claim 2 wherein the fungus is *L. sulphureus, P. ostreatus, P. sajor-caju, G. Tsujae,* or *G. lucidium*.

4. The method of claim 1 wherein the surfactant is an ionic surfactant or a mixture of an ionic and a nonionic surfactant.

5. The method of claim 1 wherein the treatment of said at least one vegetable oil is effected by a culture filtrate.

6. The method of claim 1 wherein said vegetable oil has a saturation index of less than about 1.0.

7. The method of claim 6 wherein said vegetable oil has a saturation index of less than about 0.5.

8. A method of inhibiting nematode related damage to a plant which method comprises
   the step of administering to the location, roots or seeds of said plant an effective amount of a nematicidal composition which comprises a mixture of
   a) a nematocidal product of treatment of at least one vegetable oil by a culture of, or by a filtrate from a culture of, basidiomycete or ascomycete fungi, wherein said treatment comprises mixing said oil and said culture or filtrate followed by recovering said treated oil to provide for said nematocidal product of treatment and
   b) an aqueous solution of a surfactant;
   whereby said nematode-related damage is inhibited.

9. The method of claim 5 wherein said fungus is of the genus Ganoderma, Laetiporus, Lentinus, Morchella, or Pleurotus.

10. The method of claim 9 wherein the fungus is *L. sulphureus, P. ostreatus, P. sajor-caju, G. Tsujae,* or *G. lucidium.*

11. The method of claim 8 wherein the surfactant is an ionic surfactant or a mixture of an ionic and a nonionic surfactant.

12. The method of claim 8 wherein the treatment of said at least one vegetable oil is effected by a culture filtrate.

13. The method of claim 8 wherein said vegetable oil has a saturation index of less than about 1.0.

14. The method of claim 13 wherein said vegetable oil has a saturation index of less than about 0.5.

* * * * *

UNITED STATES PATENT AND TRADEMARK OFFICE
CERTIFICATE OF CORRECTION

PATENT NO.    : 6,517,851 B1                                            Page 1 of 1
DATED         : February 11, 2003
INVENTOR(S)   : Bryan Hiromoto It is certified that error appears in the above-identified patent and that said Letters Patent is hereby corrected as shown below:

<u>Title page, Item [54] and Column 1, lines 1-2,</u>
Title, delete "REDUCING NEMATODE INFESTATION WITH FUNGI TREATED OIL"; and add -- COMPOSITION --

Signed and Sealed this

Eighth Day of June, 2004

JON W. DUDAS
*Acting Director of the United States Patent and Trademark Office*